United States Patent [19]

Bollens et al.

[11] Patent Number: 5,591,449

[45] Date of Patent: Jan. 7, 1997

[54] VESICLES, AND COSMETIC OR PHARMACEUTICAL COMPOSITIONS CONTAINING VESICLES, BOUNDED BY ONE OR MORE LAMELLAE COMPOSED OF A LIPID PHASE CONTAINING FLUORINE-CONTAINING, POLYGLYCEROLATED AMPHILIC SULPHUR COMPOUNDS

[75] Inventors: Eric Bollens, Saint Maurice; Claude Mahieu, Paris, both of France

[73] Assignee: L'Oreal, Paris, France

[21] Appl. No.: 502,463

[22] Filed: Apr. 14, 1995

Related U.S. Application Data

[62] Division of Ser. No. 99,488, Jul. 27, 1993, Pat. No. 5,459,165.

[30] Foreign Application Priority Data

Jul. 29, 1992 [FR] France .................. 92 09404

[51] Int. Cl.⁶ .................. C07C 323/12; H01F 17/42; A61K 9/127
[52] U.S. Cl. .................. 424/450
[58] Field of Search .................. 424/450; 568/38, 568/45, 46; 514/844

[56] References Cited

U.S. PATENT DOCUMENTS

| | | | |
|---|---|---|---|
| 3,759,874 | 9/1973 | Gresham | 528/70 |
| 3,872,058 | 3/1975 | Gresham | 525/70 |
| 4,310,698 | 1/1982 | Cooke | 568/46 |

FOREIGN PATENT DOCUMENTS

| | | |
|---|---|---|
| 0010523 | 4/1980 | European Pat. Off. . |
| 0165853 | 12/1985 | European Pat. Off. . |
| 2199536 | 4/1974 | France . |
| 2669023 | 5/1992 | France . |
| 2052579 | 5/1972 | Germany . |
| 2221683 | 2/1990 | United Kingdom . |

*Primary Examiner*—Nathan M. Nutter
*Attorney, Agent, or Firm*—Jacobson, Price, Holman & Stern, PLLC

[57] ABSTRACT

Fluorine-containing, polyglycerolated amphiphilic sulphur compounds, cosmetic or pharmaceutical composition containing them, preparation process and vesicles formed. The present invention relates to compound of formula (I)

$$R_f-(CH_2)_m-S-G_n-H \quad (1)$$

in which:

$R_f$ denotes a linear or branched $C_6$ to $C_{20}$ perfluoroalkyl radical or a mixture of linear or branched $C_4$ to $C_{20}$ perfluoroalkyl radicals;

m represents 0, 1 or 2;

n represents a statistical value or integer between 2 and 10;

$$-CH_2-CH-CH_2-O-, \quad -CH-CH_2-O-,$$
$$\qquad\quad | \qquad\qquad\qquad\quad\; |$$
$$\qquad\quad O \qquad\qquad\qquad\; CH_2$$
$$\qquad\quad | \qquad\qquad\qquad\quad\; |$$
$$\qquad\qquad\qquad\qquad\qquad\quad\; O$$
$$\qquad\qquad\qquad\qquad\qquad\quad\; |$$

$$-CH_2-CH-CH_2-O-, \quad -CH-CH_2-O-,$$
$$\qquad\quad\; | \qquad\qquad\qquad\;\; |$$
$$\qquad\quad OH \qquad\qquad\quad CH_2OH$$

or $$-CH_2-CH-O-$$
$$\qquad\quad\; |$$
$$\qquad\;\; CH_2OH$$

it being possible for each of the oxygen atoms to be linked to a hydrogen atom or to another unit G, to their use as surfactants and also to cosmetic or pharmaceutical compositions and vesicles containing them, and to a process for preparing them.

10 Claims, No Drawings

VESICLES, AND COSMETIC OR PHARMACEUTICAL COMPOSITIONS CONTAINING VESICLES, BOUNDED BY ONE OR MORE LAMELLAE COMPOSED OF A LIPID PHASE CONTAINING FLUORINE-CONTAINING, POLYGLYCEROLATED AMPHILIC SULPHUR COMPOUNDS

This is a divisional application of Ser. No. 08/099,488, filed Jul. 27, 1993 and now U.S. Pat. No. 5,459,165.

The present invention relates to fluorine-containing, polyglycerolated sulphur compounds which are useful, in particular, in cosmetic or pharmaceutical compositions, to a process for preparing them and also to cosmetic compositions containing these compounds as surfactants, where some of these compounds constitute nonionic amphiphilic lipids capable of forming vesicles having a lamellar structure.

In the cosmetics field, in particular, it is known to use perfluoropolyethers in processes for cleansing, protecting and making-up the skin or alternatively for washing the hair.

The Applicant has now discovered new compounds which possess surfactant properties, as an emulsifier or dispersing or foaming agent, and some of which have the capacity to form vesicles exhibiting a good persistence of effect, in contrast to other perfluoro(methyl isopropyl ether)s, in particular those known by the name of "FOMBLIN" perfluoro(methyl isopropyl ether)s.

Thus, the present invention relates to the compounds of formula:

$$R_f-(CH_2)_m-S-G_n-H \quad (1)$$

in which:

$R_f$ denotes a linear or branched $C_6$ to $C_{20}$ perfluoroalkyl radical or a mixture of linear or branched $C_4$ to $C_{20}$ perfluoroalkyl radicals;

m represents 0, 1 or 2;

n represents a statistical value or integer between 2 and 10;

G represents a unit chosen from:

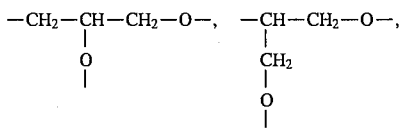

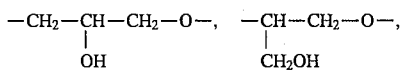

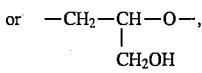

it being possible for each of the oxygen atoms to be linked to a hydrogen atom or to another unit G.

Preferred compounds are those for which $R_f$ denotes a linear or branched $C_6$ to $C_{14}$ perfluoroalkyl radical and m is 2.

The compounds of formula (I) according to the invention, including those for which m is 0, may be prepared by carrying out the reaction of a fluorine-containing mercaptan of formula (II):

$$R_f-(CH_2)_m-S-H \quad (II)$$

in which $R_f$ and m have the same meanings as in the formula (I), in the presence of an active amount of basic catalyst, by condensation a) with n mol
of glycidol, or
of a compound containing an epoxide function which is capable, after reaction, of regenerating an alcohol function,
optionally followed by a neutralization; or b) with glycidyl isopropylideneglyceryl ether, when n, an integer, is equal to 2 or a multiple of 2,
optionally followed by a hydrolysis; or c) with glycidyl diisopropylidenetriglyceryl ether, when n is an integer equal to 4,
optionally followed by a hydrolysis.

The basic catalyst used can be, in particular, chosen from alkali metal hydroxides, alkali metal alcoholates such as sodium methylate or potassium tertburylate, alkali metal hydrides such as sodium hydride and tertiary amines such as pyridine or triethylamine. They can also be Lewis bases, among which caesium, rubidium and potassium fluorides may be mentioned. These catalytic compounds may also be supported on a solid such as alumina. Preferably, an alkali metal alcoholate such as potassium tert-butylate or sodium methylate is used.

According to the invention, the concentration of catalyst employed is between 1 and 20 mol %, and preferably between 5 and 10 mol %, relative to the fluorine-containing mercaptan of formula (II) used.

As a solvent for carrying out the reaction, a choice may be made, in particular, from aromatic hydrocarbons such as toluene, cumene, ortho-xylene, metaxylene, para-xylene and mixtures thereof.

The fluorine-containing mercaptan of formula (II) may be mixed first with the basic catalyst. To carry out the mixing, it is possible to work at a temperature of between 40° and 160° C., and preferably between 60° and 140° C. It is possible to work under an inert atmosphere. Inert atmosphere is understood to mean a gaseous reaction mixture essentially containing nitrogen, argon, helium and mixtures thereof.

Glycidol is then added to the mixture obtained. The addition may be performed all at once, or gradually over a period of time which can range from 30 minutes to 2 hours, for example.

At the end of the reaction, it may, in addition, be necessary to neutralize the mixture obtained using an inorganic or organic acid.

As envisaged above, the same compounds may be prepared using a compound containing an epoxide function which is capable, after reaction, of regenerating an alcohol function, and the epoxide can be, in particular, epichlorohydrin, t-butyl glycidyl ether or benzyl glycidyl ether.

In a second variant of the process, for the case where n is an integer equal to 2 or a multiple of 2, the corresponding compounds of formula (I) may be prepared by reacting the corresponding fluorine-containing mercaptan of formula (II) with glycidyl isopropylideneglyceryl ether under the same conditions as those described above.

Similarly, in a third variant, for the compounds in which n is an integer equal to 4, the corresponding compounds of formula (I) may be prepared by equimolar reaction of the corresponding fluorine-containing mercaptan of formula (II) with glycidyl diisopropylidenetriglyceryl ether under the same conditions as those described above.

In these latter two cases, it is possible either to purify the unhydrotysed intermediate compound, which undergoes a hydrolysis reaction in a second stage, or not to purify it, the product then being purified after hydrolysis of the intermediate compound. The purification can be carried out, for example, by distillation.

The hydrolysis reaction may be performed in the presence of an inorganic acid such as hydrochloric, sulphuric or phosphoric acid, or alternatively in the presence of an organic acid such as acetic, lactic or methanesulphonic acid. The reaction medium can then be neutralized, if necessary, using a base such as sodium hydroxide or potassium hydroxide.

The compounds of formula (I) according to the invention can take the form of an oil or the form of a paste or solid at room temperature. These compounds are soluble or dispersible in water. They possess, in addition, foaming, emulsifying or dispersing properties.

Another subject of the invention relates to the use of the products of formula (I) as surfactants. They can be used, in particular, in cosmetic compositions for the skin and the exoskeleton or in pharmaceutical or dermopharmaceutical compositions.

Thus, the invention also relates to cosmetic or pharmaceutical compositions containing at least one compound of formula (I):

in which:

$R_f$ denotes a linear or branched $C_6$ to $C_{20}$ perfluoroalkyl radical or a mixture of linear or branched $C_4$ to $C_{20}$ perfluoroalkyl radicals;

m represents 0, 1 or 2;

n represents a statistical value or integer between 2 and 10;

G represents a unit chosen from:

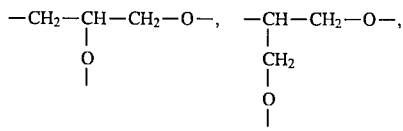

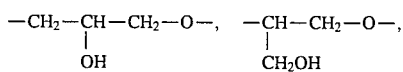

or 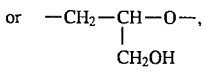

it being possible for each of the oxygen atoms to be linked to a hydrogen atom or to another unit G.

These compositions can take the form of emulsions, microemulsions, milks or creams, lotions, gels, solid sticks, pastes, sprays or aerosol foams.

In these compositions, the compounds of formula (I) represent from 0.1 to 50%, and preferably 0.1 to 25%, by weight of the total weight of the composition.

In the compositions according to the invention, the compounds of formula (I) may be combined with other ionic or nonionic surface-active agents, with natural or synthetic, ionic or nonionic polymers, with oils or waxes, with more or less hydrolysed proteins, with thickeners, with pearlescence agents, with emollients, with hydrating agents, with colorants, with reducing or oxidizing agents, with preservatives, with perfumes, with anti-UV screening agents, with solvents, with propellants or with pharmaceutically or parapharmaceutically active products.

Among oils, there may be mentioned, without implied limitation, mineral oils such as liquid paraffin, animal oils such as whale, seal, halibut-liver, cod-liver, tuna and mink oils, vegetable oils such as almond, groundnut, wheat germ, maize, olive, jojoba, sesame and sunflower oils, silicone oils and partially or fully perfluorinated oils such as perfluorodecalin, perfluoroalkyl bromides such as perfluorooctyl bromide and the perfluoro(methyl isopropyl ether)s known by the name of "FOMBLIN HC" and marketed by the company MONTEFLUO.

Among waxes, there may be mentioned, without implied limitation, sipol wax, lanolin, hydrogenated lanolin, acetylated lanolin, beeswax, candelilla wax, microcrystalline wax, paraffin, carnauba wax, spermaceti, cocoa butter, shea butter, silicone waxes and hydrogenated oils which are solid at 25° C. The oils and waxes may also be chosen from the esters of saturated or unsaturated $C_{12}$ to $C_{22}$ fatty acids and of lower polyols or alcohols such as isopropanol, glycol or glycerol, or of saturated or unsaturated, linear or branched $C_8$–$C_{22}$ fatty alcohols, or alternatively of $C_{10}$–$C_{22}$ 1,2-alkanediols.

When the compositions take the form of an emulsion water-in-oil or oil-in-water type, the compounds of formula (I) may be combined with other traditional emulsifying agents such as polyoxyethylenated fatty acids or fatty alcohols, potyglycerol alkyl ethers, esters of fatty acid and of sorbitan, polyoxyethylenated or otherwise, esters of fatty acid and of sorbitol, polyoxyethylenated or otherwise, polyoxyethylenated castor oil, salts of fatty acids and of amines or of multivalent metals, alkyl sulphates, polyoxyethylenated or otherwise, and alkyl phosphates, polyoxyethylenated or otherwise.

The cosmetic or pharmaceutical compositions according to the invention can take the form of shampoos or aftershampoo products, foam baths, cleansing compositions, baths or creams for skin and hair care, antisun compositions, shaving creams or foams, aftershave lotions, body deodorants, compositions for buccodental use, hair dyeing compositions, skin colouring compositions or alternatively make-up compositions, for example.

The Applicant demonstrated, in addition, that some compounds of formula (I), and especially the compounds of formula (I) for which $R_f$ represents a linear $C_6$ to $C_{10}$ perfluoroalkyl radical, m is equal to 2 and n represents a statistical value or integer between 2 and 3, are nonionic amphiphilic lipids capable of forming vesicles having a lamellar structure.

In a known manner, these vesicles are characterized by a structure in the form of lamellae consisting of layers of lipid phase encapsulating an aqueous phase.

These vesicles are, in a known manner, prepared in the form of a dispersion, in an aqueous phase. A nonlimiting list of various methods of preparation will be found in "Les liposomes en biologie cellulaire et pharmacologie" [Liposomes in cell biology and pharmacology] Editions INSERM—John LIBLEY, Eurotext, 1987, pages 6 to 18.

The vesicles obtained hence consist of a lipid phase consisting of one or more lamellae encapsulating an aqueous phase E, and they are dispersed in an aqueous dispersion phase D.

The vesicles formed with the compounds of formula (I) for which $R_f$ represents a linear $C_6$–$C_{10}$ perfluoroalkyl radical, m is equal to 2 and n represents a statistical value or integer between 2 and 3 possess, in the main, a good degree of swelling, low permeability and good stability.

The subject of the present invention is also vesicles having a lamellar structure, bounded by one or more lamellae composed of a lipid phase encapsulating an aqueous phase and containing at least one compound of formula (I) for which $R_f$ represents a linear $C_6$–$C_{10}$ perfluoroalkyl radical, m is equal to 2 and n is a statistical value or integer between 2 and 3.

Surprisingly, it was found that a composition containing a vesicular dispersion prepared with the compounds according to the invention exhibits a good water-resistant persistent effect after application to the skin. A preferred cosmetic application of these vesicular dispersions hence relates to artificial colouring products for the skin and antisun products.

The subject of the present invention is hence also a cosmetic or pharmaceutical composition containing, dispersed in an aqueous dispersion phase D, vesicles bounded by one or more lamellae composed of a lipid phase containing at least one compound of formula (I) in which $R_f$ represents a linear $C_6$–$C_{10}$ perfluoroalkyl radical, m is equal to 2 and n represents a statistical value or integer between 2 and 3.

According to the invention, all ionic and/or nonionic amphiphilic lipids capable of forming stable vesicles, alone or mixed with additives whose function is to decrease the permeability of the membranes of the vesicles and to improve their stability, may be used mixed with the compounds of formula (I) to constitute the lipid membranes of the vesicles according to the invention. The lipid phase constituting the membranes of the vesicles of the dispersion according to the invention can hence comprise, in a known manner, at least one lipid chosen from the group composed of:

A/ the nonionic lipids defined below:
(1) the linear or branched glycerol derivatives of formula:

$$R_o O\text{—}[C_3H_5(OH)O]_q\text{—}H \qquad (II)$$

in which:

—$C_3H_5(OH)O$— is represented by the following structures, taken mixed or separately:

—CH₂CHOHCH₂O—,   —CH₂—CHO—   or   —CH—CH₂O—
                        |                    |
                        CH₂OH              CH₂OH q is an average statistical value between 1 and 6, or alternatively q=1 or 2, in which case —$C_3H_5(OH)O$— is represented by the structure —CH₂—CHOH—CH₂O;

$R_o$ represents:
(a) a saturated or unsaturated, linear or branched aliphatic chain containing from 12 to 30 carbon atoms; or hydrocarbon radicals of lanolin alcohols; or the residues of long-chain alpha-diols;
(b) a residue $R_1$CO, where $R_1$ is a linear or branched $C_{11}$–$C_{29}$ aliphatic radical;
(c) a residue $R_2$—[OC₂H₃($R_3$)]— where:
$R_2$ can assume the meaning (a) or (b) given for $R_o$;
—OC₂H₃($R_3$)— is represented by the following structures, taken mixed or separately:

—OCH—CH₂—   and   —O—CH₂—CH—
     |                        |
     $R_3$                    $R_3$ where $R_3$ assumes the meaning (a) given for $R_o$;
(2) linear or branched polyglycerol ethers containing two fatty chains;
(3) fatty-chain diols;
(4) fatty alcohols, oxyethylenated or otherwise, sterols such as β-sitosterol, cholesterol and phytosterols, oxyethylenated or otherwise;
(5) ethers and esters of polyols, oxyethylenated or otherwise, it being possible for the linkage of the ethylene oxide moieties to be linear or cyclic;
(6) glycolipids of natural or synthetic origin, ethers and esters of mono- or polysaccharides and, in particular, glucose ethers and esters;
(7) the hydroxyamides represented by the formula:

$$R_4\text{—CHOH—CH—COA} \qquad (III)$$
$$\phantom{R_4\text{—CHOH—}} |$$
$$\phantom{R_4\text{—CHOH—}} R_5\text{—CONH}$$

in which:
$R_4$ denotes a $C_7$–$C_{21}$ alkyl or alkenyl radical;
$R_5$ denotes a saturated or unsaturated $C_7$–$C_{31}$ hydrocarbon radical;
COA denotes a group chosen from the following two groups:
a residue

CON—B
 |
 $R_6$ where:
B is an alkyl radical derived from mono- or polyhydroxylated primary or secondary amines; and
$R_6$ denotes a hydrogen atom or a methyl, ethyl or hydroxyethyl radical; and
a residue —COOZ, where Z represents the residue of a $C_3$–$C_7$ polyol;
(8) natural or synthetic ceramides;
(9) dihydroxyalkylamines, oxyethylenated fatty amines;
(10) the glycerol derivatives described in Patent Application PCT No. 92/08,685 and corresponding to the formula:

$$CH_2\text{—CH—}CH_2\text{—O}\left[\text{—}CH_2\text{—CH—O—}\right]_p\text{H} \qquad (IV)$$
$$\phantom{CH_2\text{—}} | \phantom{\text{—CH—}CH_2\text{—O}\left[\text{—}CH_2\text{—}}} |$$
$$\phantom{CH_2\text{—}} OH\ OH \phantom{\text{—CH—}CH_2\text{—O}\left[\text{—}CH_2\text{—}}} R_7$$

in which $R_7$ represents a linear $C_{14}$ to $C_{18}$ alkyl radical or a group —CH₂Y in which Y is —O$R_8$, $R_8$ representing a linear $C_{10}$–$C_{18}$, and preferably $C_{16}$, alkyl radical, and p represents an average statistical value greater than 1 and not more than 3, and, in addition, when $R_7$ is —CH₂Y, p can also represent an integer equal to 2.

B/ the ionic amphiphilic lipids defined below:
(1) the following anionic amphiphilic lipids:
natural phospholipids, chemically or enzymatically modified phospholipids and synthetic phospholipids;
the anionic compounds of formula:

$$R_9\text{—CHOH—CH—COO}M_1 \qquad (V)$$
$$\phantom{R_9\text{—CHOH—}} |$$
$$\phantom{R_9\text{—CHO}} R_{10}\text{CONH}$$

in which:
$R_9$ represents a $C_7$–$C_{21}$ alkyl or alkenyl radical;
$R_{10}$ represents a saturated or unsaturated $C_7$–$C_{31}$ hydrocarbon radical, and
$M_1$ represents H, Na, K, NH₄ or a substituted ammonium ion derived from an amine;
anionic compounds such as the phosphoric esters of fatty alcohols, in particular dicetyl phosphate and dimyristyl phosphate in the form of acids or of alkali metal salts; heptylnonylbenzenesulphonic acid; cholesterol acid sulphate or cholesterol acid phosphate, as well as their alkali metal salts; lysolecithins; alkyl sulphates such as sodium cetyl sulphate; gangliosides;

(2) the following cationic amphiphilic lipids;
the cationic compounds having the formula:

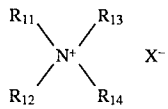 (VI)

in which $R_{11}$ and $R_{12}$, which may be identical or different, represent $C_{12}$–$C_{10}$ alkyl radicals and $R_{13}$ and $R_{14}$, which may be identical or different, $C_1$—$C_4$ alkyl radicals;

long-chain amines and their quaternary ammonium derivatives; the esters of long-chain amino alcohols and their salts and quaternary ammonium derivatives; and polymerizable lipids, as described by RINGSDORF et al. in "Angewandte Chemie.", vol. 27, No. 1, January 1988, pages 129–137.

Additives, for instance certain polymers such as, for example, polypeptides and proteins, may also be added to the lipid phase constituting the vesicular walls.

The aqueous dispersion phase according to the invention can consist of water, or a mixture of water and at least one water-miscible solvent such as $C_1$–$C_7$ alcohols and $C_1$–$C_5$ alkyl polyols. The aqueous phase can also contain compounds in solution, such as sugars, organic or inorganic salts or polymers. The aqueous dispersion phase can also contain a dispersion of droplets of a water-immiscible liquid which the vesicles stabilize, so that it is not necessary to introduce an emulsifier such as glycerol monostearate, for example, for this stabilization; this water-immiscible liquid may be chosen from the group composed of animal or vegetable oils, natural or synthetic essential oils, hydrocarbons, halocarbons, silicones, esters of an inorganic acid and of an alcohol, ethers and polyethers. Examples of water-immiscible liquids are mentioned in European Patent 455,528.

In the composition according to the invention, the total lipid phase of the dispersion advantageously represents between 0.01% and 50% by-weight, and preferably between 1 and 20% by weight, relative to the total weight of the dispersion. The amphiphilic lipid(s) advantageously represent(s) between 10 and 95% by weight, and preferably from 40 to 90% by weight, relative to the total weight of the vesicular lipid phase. The vesicles are preferably between 20 and 3000 nanometers, and more especially between 20 and 500 nanometers, in size.

The compositions obtained with the compounds according to the invention can contain, in a known manner, one or more active compound(s) having cosmetic and/or dermopharmaceutical activity, which, depending on their solubility properties, can have different locations. For example, in the case of dispersions of vesicles containing an encapsulated aqueous phase, if the active compounds are fat-soluble, they are introduced into the lipid phase constituting the lamella(e) of the vesicles or into the droplets of water-immiscible liquid stabilized by the vesicles; if the active compounds are water-soluble, they are introduced into the encapsulated aqueous phase of the vesicles or into the aqueous dispersion phase; if the active compounds are amphiphilic, they distribute between the lipid phase and the encapsulated aqueous phase, with a partition coefficient which varies according to the nature of the amphiphilic active compound and the respective compositions of the lipid phase and of the encapsulated aqueous phase. Generally speaking, the active compounds are sited in the lipid phase of the lamellae and/or in the phase encapsulated by the lamellae.

In the case of emulsions of the oil-in-water or water-in-oil type containing a compound of formula (I) as an emulsifying agent, the fat-soluble compounds are introduced into the oily phase and the water-soluble compounds into the aqueous phase. Similarly, the amphiphilic active compounds distribute between the aqueous phase and the oily phase.

As cosmetic and/or dermopharmaceutical active compounds, there may be mentioned antioxidants or anti-free radical agents, hydrating or humectant agents, melanoregulatory agents which accelerate tanning, depigmenting melanoregulatory agents, skin colouring agents, liporegulators, anti-aging and antiwrinkle agents, anti-UV agents, keratolytic agents, emollients, anti-inflammatory agents, refreshing agents, cicatrizing agents, vascular protective agents, antibacterial agents, antifungal agents, insect-repellant agents, antiperspirant agents, deodorant agents, antidandruff agents, agents for combating hair loss, hair colorants, hair bleaching agents, reducing agents for permanent-waving, and skin and hair conditioning agents. These cosmetic and/or dermopharmaceutical active compounds are mentioned in greater detail in Patent Application PCT No. 92/08,685.

The compositions according to the invention can also contain, in a known manner, formulation additives having neither cosmetic activity nor dermopharmaceutical activity of their own, but which are useful for the formulation of compositions in the form of a lotion, cream or serum. These additives are, in particular, taken from the group composed of gelling agents, polymers, preservatives, colorants, opacifiers and perfumes. Among the gelling agents which can be used, there may be mentioned cellulose derivatives such as hydroxyethyl cellulose, derivatives of algae such as satiagum, natural gums such as tragacanth, and synthetic polymers, especially the mixtures of polyvinylcarboxylic acids marketed under the trade name "CARBOPOL" polymers by the company GOODRICH. These additives are, more especially, added to an aqueous phase, for example the aqueous phase of dispersion of vesicles or the aqueous phase of an oil-in-water or water-in-oil emulsion.

The examples given below by way of illustration and without implied limitation will enable a better understanding of the invention to be gained.

PREPARATION EXAMPLES

Example 1

Compound of formula (I) for which $\bar{n}=3$, $R_f=C_8F_{17}$ and $m=2$ 108 g (0.225 mol) of 2-F-octylethanethiol are introduced into a reactor under an inert atmosphere. 1.26 g of potassium tert-butylate (11.25 meq) are added with stirring and at a temperature of 25° C. The temperature is brought to between 50° and 60° C. and the assembly is placed under a vacuum of 4000 Pa in order to remove the tert-butanol. Raising of the temperature is continued. When 80° C. is reached, 16.65 g of glycidol (0.225 mol) are added in the course of 30 minutes while the temperature is maintained in the region of 80° C. The reaction medium becomes pasty. In order to make the mixture fluid, 59 g of xylene are added in the course of 15 minutes. Heating is resumed until the temperature reaches 130° C.

At this temperature, 33.3 g of glycidol (0.45 mol) are added dropwise in the course of 75 minutes. When the addition is complete, the temperature is maintained at 130° C. for 15 minutes. Raising of the temperature is resumed to 155° C., and the xylene is removed by distillation at atmospheric pressure.

After 15 minutes at 155° C., the medium is neutralized with 11.5 ml of 1N HCl. A few foams form, the mixture then becomes translucent and the temperature has dropped to 135° C. At this temperature, the product is left for approximately 15 minutes under 4000 Pa, and it then solidifies at room temperature.

157 g of product are obtained.

Melting point: 64° C.

ELEMENTAL ANALYSIS

|  | % C | % H | % S | % F |
|---|---|---|---|---|
| Calculated | 32.48 | 3.27 | 4.56 | 46.01 |
| Found | 32.47 | 3.27 | 4.28 | 46.16 |

Example 2

Compound of formula (I) in which $\bar{n}=2.5$, $R_f=C_8F_{17}$ and m=2

According to a process equivalent to that of Example 1, the compound of Example 2 is prepared by condensing 108 g of 2-F-octylethanethiol with 41.63 g of glycidol. 150 g of product are obtained.

Melting point: 71° C.

ELEMENTAL ANALYSIS

|  | % C | % H | % S | % F |
|---|---|---|---|---|
| Calculated | 31.58 | 3.01 | 4.81 | 48.57 |
| Found | 31.62 | 3.22 | 4.60 | 48.61 |

Example 3

Compound of formula (I) for which n=2, $R_f=C_8F_{17}$ and m=2
1-(F-octyl)-5,9,10-trihydroxy-7-oxa-3-thiadecane a) Preparation of (2'-F-octylethylthio)-3-(isopropylideneglyceryl)-2-propanol 192 g of 2-F-octylethanethiol (0.4 mol) are introduced at a temperature of 25° C. into a reactor; 3.61 g (20 meq) of a solution of sodium methylate dissolved in methanol (titre: 5.54 meq/g) are added under an inert atmosphere. The mixture is heated under a vacuum of 4000 Pa in order to remove the methanol.

The reaction mixture then possesses a milky appearance. The temperature in the flask when evaporation of the methanol is complete is 68°–70° C. Glycidyl isopropylideneglyceryl ether (75.2 g–0.4 mol) is then added dropwise in the course of 1 hour after the heating has been stopped. The exothermic reaction maintains the temperature at between 65° and 68° C. The mixture is stirrred for a further two hours at a temperature of 25° C.

The product is purified by distillation: b.p.=159° C./66.6 Pa.

ELEMENTAL ANALYSIS

|  | % C | % H | % S | % F |
|---|---|---|---|---|
| Calculated | 34.14 | 3.17 | 4.80 | 48.32 |
| Found | 34.11 | 3.22 | 4.58 | 48.07 | b) Hydrolysis of (2'-F-octylethylthio)-3-(isopropylideneglyceryl)-2-propanol 85 g (0.127 mol) of the product obtained in Example 3a), dissolved in 65 ml of isopropanol, are introduced into a reactor. At a temperature of 25° C., 3.5 ml of concentrated (33%) hydrochloric acid are added dropwise in the course of 15 minutes.

The mixture is brought to a temperature of 60° C. for 7 hours.

The medium is then neutralized with 10% sodium hydroxide solution. After evaporation of the solvents and return to room temperature, the mixture is taken up in isopropanol and then filtered. After evaporation of the filtrate, 68 g of a tacky white solid are obtained.

Melting point: 87° C.

ELEMENTAL ANALYSIS

|  | % C | % H | % S | % F |
|---|---|---|---|---|
| Calculated | 30.57 | 2.70 | 5.10 | 51.43 |
| Found | 30.53 | 2.76 | 4.96 | 51.62 |

Example 4

Compound of formula (I) for which n=2, $R_f=C_6F_{13}$ and m=2
1-(F-hexyl)-5,9,10-trihydroxy-7-oxa-3-thiadecane a) Preparation of 1-(2'-F-hexylehylthio)-3-(isopropylideneglyceryl)-2-propanol According to the procedure described in Example 3a), the compound is prepared by reacting 152 g of 2-F-hexylethanethiol with 75.2 g of glycidyl isopropylideneglyceryl ether.

The product is purified by distillation: b.p. =140° C./67 Pa.

112 g of a transparent liquid are obtained.

ELEMENTAL ANALYSIS

|  | % C | % H | % S | % F |
|---|---|---|---|---|
| Calculated | 35.92 | 3.72 | 5.64 | 43.45 |
| Found | 35.06 | 3.60 | 5.40 | 43.01 | b) Hydrolysis of 1-(2'-F-hexylethylthio)-3'-(isopropylideneglyceryl)-2-propanol 85 g (0.15 mol) of the product obtained in Example 4a), dissolved in 65 ml of isopropanol, are introduced into a 250-ml reactor. At 25° C., 7.2 ml of concentrated hydrochloric acid are added in the course of 15 minutes.

The mixture is heated to 60° C. for 7 hours. The medium is then neutralized with 10% sodium hydroxide solution. After evaporation of the solvents and return to a temperature of 25° C., the mixture is taken up in isopropanol and then filtered. After evaporation of the filtrate, 78 g of a translucent amorphous product are obtained.

Melting point: 65° C.

ELEMENTAL ANALYSIS

|  | % C | % H | % S | % F |
|---|---|---|---|---|
| Calculated | 31.83 | 3.24 | 6.07 | 46.75 |
| Found | 31.63 | 3.48 | 5.74 | 46.41 |

Example 5

Compound of formula (I) in which n=4, $R_f=C_8F_{17}$ and m=2
1-[(1',3'-diglyceryl)-2'-glyceryl]-3-(2"-F-octylethylthio)glycerol 192 g (0.4 mol) of 2-F-octylethanethiol are introduced at 25° C. into a 500-ml reactor, and 2.24 g (20 meq) of potassium tert-butylate are added under a nitrogen atmosphere. The mixture is brought to 60° C., and the tert-butanol formed is evaporated off under a vacuum of 2000 Pa for 10 minutes. At this temperature, 150.4 g (0.4 mol) of glycidyl diisopropylidene triglyceryl ether are added in the course or one hour.

After return to 25° C., the mixture is hydrolysed with a solution of 40 ml of concentrated hydrochloric acid in 200 ml of isopropanol. This solution is added in the course of 10 minutes to the reaction mixture, which is heated to 50° C. for three hours.

After return to 25° C., the solution is neutralized with 12N NaOH solution.

The mixture is then filtered and the amber-coloured filtrate is concentrated under vacuum. The viscous mass thereby obtained, taken up in 200 ml of isopropanol, is filtered again.

After evaporation of the solvent under vacuum, the residue is purified on Merck 60H silica (eluent $CH_2Cl_2/CH_3OH$, 90:10) to yield 150 g of product in the form of an oil.

ELEMENTAL ANALYSIS

|  | % C | % H | % S | % F |
| --- | --- | --- | --- | --- |
| Calculated | 34.03 | 3.76 | 4.13 | 41.49 |
| Found | 33.85 | 3.72 | 4.22 | 41.36 |

Example 6

Compound of formula (I) in which $\bar{n}$=5, $R_f=C_8F_{17}$ and m=2

According to the same process as that described in Example 1, 72 g (0.15 mol) of 2-F-octylethanethiol are condensed with 11.1 g (0.15 mol) of glycidol in the presence of 0.85 g of potassium tert-butylate at 80° C. Then, after 60 g of xylene have been added, 44.4 g (0.6 mol) of glycidol are added at 130° C.

When the reaction is complete, the mixture is neutralized with 7.5 ml of normal HCl.

125 g of a product are obtained in the form of a paste, the melting point of which is approximately 47.5° C.

ELEMENTAL ANALYSIS

|  | % C | % H | % S | % F |
| --- | --- | --- | --- | --- |
| Calculated | 35.30 | 4.15 | 3.77 | 37.97 |
| Found | 35.12 | 4.41 | 3.65 | 37.28 |

Example 7

Compound of formula I) in which $\bar{n}$=5, $R_f=C_6F_{13}$ and m=2

Under the conditions described in Example 1, 57 g (0.15 mol) of 2-F-hexylethanethiol are condensed with 11.1 g (0.15 mol) of glycidol in the presence of 0.85 g (7.5 meq) of potassium tert-butylate at 80° C. Then, after 60 g of xylene have been added, 44.4 g (0.6 mol) of glycidol are added at 130° C. After evaporation of the solvent and neutralization, the product is dried at 155° C.

112 g of a solid are obtained in the form of a paste, the melting point of which is approximately 43.4° C.

ELEMENTAL ANALYSIS

|  | % C | % H | % S | % F |
| --- | --- | --- | --- | --- |
| Calculated | 36.80 | 4.70 | 4.27 | 32.91 |
| Found | 36.86 | 4.97 | 4.09 | 32.89 |

EXAMPLES

Compound of formula (I) in which $\bar{n}$=10, $R_f=C_6F_{13}$ and m=2

135.7 g (3.57 mol) of 2-F-hexylethanethiol are introduced into a reactor placed under an inert atmosphere. 2 g of potassium tert-butylate (17.85 meq) are added with stirring and at room temperature (25° C.). The temperature is brought to between 50° and 60° C. and the assembly is placed under a vacuum of 2666 Pa to remove the tert-butanol formed. 150 g of xylene are added at this temperature. Raising of the temperature is continued. When 80° C. is reached, 26.4 g (0.357 mol) of glycidol are added in the course of 15 minutes. The temperature is brought to 130° C. in the course of 60 minutes. At this temperature, 237.9 g of glycidol are added in the course of 30 minutes. When the addition is complete, the mixture is maintained at 130° C. for 15 minutes.

Raising of the temperature is resumed to 155° C., and the xylene is then removed by distillation, first at atmospheric pressure and then under reduced pressure at 2666 Pa. After 20 minutes at 155° C., the mixture is neutralized with 18 ml of normal hydrochloric acid.

The product is left for 15 minutes under 2666 Pa at 135° C. After cooling to 25° C., 395 g of product which takes the form of a very viscous amber-coloured oil are obtained.

ELEMENTAL ANALYSIS

|  | % C | % H | % S | % F |
| --- | --- | --- | --- | --- |
| Calculated | 40.72 | 5.84 | 2.86 | 22.03 |
| Found | 40.24 | 6.53 | 2.67 | 21.78 |

In Examples 1, 2, 6, 7 and 8, $\bar{n}$ represents a statistical value and is determined by the mole ratio of glycidol to mercaptan.

FORMULATION EXAMPLES

Example 1

Coloured Cream

The following products are weighed into a glass beaker:

| Compound of Example 1 | 14 g |
| --- | --- |
| Cholesterol | 4 g |
| Dicetyl phosphate | 2 g |

Mixing of these three products is carried out by melting at a temperature of 100° C. under a nitrogen atmosphere. The temperature of the molten mixture is then brought down to 90° C. 20 g of water containing 7 g of caramel, marketed by the company CERESTAR under the name "CERESTAR CARAMEL 15610", are then added, and the mixture obtained is homogenized at a temperature of 90° C.

34.65 g of water containing 13 g of caramel are then added.

At a temperature of 70° C., the mixture is homogenized using a Virtis type ultradisperser for 4 minutes at a speed of 40,000 rpm.

Lastly, 5 g of water containing 0.3 g of preservative consisting of diazolidinylurea, sold under the name "GERMAL II" by the company SUTTON, and 0.05 g of preservative consisting of a mixture of methylchloroisothiazolinone and methylisothiazolinone, sold under the name "KATHON CG" by the company ROHM & HAAS, are added.

A dispersion of thick vesicles, brown in colour, is thereby obtained.

Example 2

Artificial Tanning Cream

According to the procedure of Example 1, the following are produced:

1st phase:

| | |
|---|---|
| Compound of Example 1 | 6 g |
| Cholesterol | 1.6 g |
| Monosodium stearoylglutamate sold under the name "ACYL GLUTAMATE HS11" by the company AJINOMOTO | 0.4 g |
| Dihydroxyacetone | 3 g |
| Caramel sold under the name "CERESTAR CARAMEL 15610" by the company CERESTAR | 3 g |
| Water | 40 g |
| Mixture of methylchloroisothiazolinone and methylisothiazolinone, sold under the name "KATHON CG" by the companyy ROHM & HAAS | 0.1 g |
| Diazolidinylurea sold under the name "GERMAL II" by the company SUTTON | 0.3 g |
| Water | 5 g |

2nd phase:

The following are added to the vesicular phase obtained above:

| | |
|---|---|
| Macadamia oil | 15 g |
| Volatile silicone oil | 10 g |

At a temperature of 30° C., the whole is homogenized using a Virtis ultradisperser for 4 minutes at a speed of 40,000 rpm.

Lastly, the following are added:

| | |
|---|---|
| Ether of cetyl alcohol and of hydroxyethylcellulose, sold under the name "NATROSOL PLUS CS" by the company AQUALON | 0.7 g |
| Methyl para-hydroxybenzoate | 0.2 g |
| Water | qs 100 g |

A thick cream is thereby obtained.

Example 3

Antisun Care Milk

According to the procedure of Example 2, the product of the following composition is prepared:

| | |
|---|---|
| Compound of Example 1 | 4.5 g |
| Cholesterol | 1.2 g |
| Dicetyl phosphate | 0.3 g |

-continued

| | |
|---|---|
| Vitamin E acetate | 0.3 g |
| Glycerol | 3 g |
| Water | 40 g |
| Mixture of methylchloroisothiazolinone and methylisothiazolinone, sold under the name "KATHON CG" by the company ROHM & HAAS | 0.1 g |
| Diazolidinylurea sold under the name "GERMAL II" by the company SUTTON | 0.3 g |
| Water | 5 g |
| Liquid paraffin | 15 g |
| 2-Ethylhexyl para-dimethylaminobenzoate | 3 g |
| Crosslinked polyacrylic acid sold under the name "CARBOPOL 940" by the company GOODRICH | 0.42 g |
| Methyl para-hydroxybenzoate | 0.2 g |
| Triethanolamine | 0.4 g |
| Water | qs 100 g |

Example 4

Vitamin-Containing Anti-Aging Care Cream

According to the procedure of Example 2, the product of the following composition is prepared:

| | |
|---|---|
| Compound of Example 4 | 1.8 g |
| Cholesterol | 0.6 g |
| Cholesterol sodium sulphate | 0.6 g |
| Vitamin E acetate | 0.15 g |
| Vitamin A palmitrate | 0.15 g |
| Glycerol | 5 g |
| Magnesium ascorbate phosphate | 0.1 g |
| Propylene glycerol | 3 g |
| Water | 40 g |
| Diazolidinylurea sold under the name "GERMAL II" by the company SUTTON | 0.1 g |
| Mixture of methylchloroisothiazolinone and methylisothiazolinone, sold under the name "KATHON CG" by the company ROHM & HAAS | 0.05 g |
| Silicone oil | 1 g |
| Crosslinked polyacrylic acid sold under the name "CARBOPOL 940" by the company GOODRICH | 0.25 g |
| Methyl para-hydroxybenzoate | 0.1 g |
| Triethanolamine | 0.2 g |
| Water | qs 100 g |

Example 5

Aftershave Balm

The following vesicular dispersion is prepared:

| | |
|---|---|
| Compound of Example 1 | 1.9 g |
| Cholesterol | 1.9 g |
| Monosodium stearoylglutamate sold under the name "ACYL GLUTAMATE HS 11" by the company AJINOMOTO | 0.2 g |
| Allantoin | 0.1 g |
| Ethylmaltol | 0.4 g |
| Vinylcarboxylic polymer sold under the name "CARBOPOL 940" by the company GOODRICH | 0.25 g |
| Methyl para-hydroxybenzoate | 0.1 g |
| 1,3-Dimethylol-5,5-dimethylhydantoin sold under the name "GLYDANT" by the company GLYCO | 0.055 g AS |
| Demineralized water | qs 100 g |

Example 6

Sun-Protection Formulation
The following vesicular dispersion is prepared:

| | |
|---|---|
| Compound of Example 1 | 3.8 g |
| Cholesterol | 3.8 g |
| Dihexadecyl phosphate | 0.4 g |
| Glycerol | 2 g |
| Liquid paraffin | 15 g |
| 2-Ethylhexyl para-methoxycinnamate | 5 g |
| 2-Hydroxy-4-methoxybenzophenone | 2 g |
| Vinyl carboxylic polymer sold under the name "CARBOPOL 940" by the company GOODRICH | 0.4 g |
| Triethanolamine | qs pH 6.5 |
| Preservatives | qs |
| Perfume | qs |
| Demineralized water | qs 100 g |

Example 7

Oil-In-Water Emulsion

| Phase A | |
|---|---|
| Hydrogenated polyisobutylene | 6.5 g |
| Octyl palmitate | 5 g |
| Volatile silicone oil sold under the name "VOLATIL SILICONE 7158" by the company UNION CARBIDE | 5 g |
| Cetyl alcohol | 4 g |
| Glycerol monostearate | 3 g |
| Polyethylene glycol stearate containing 40 mol of ethylene oxide, sold under the name "MYRJ 52" by the company ICI | 2 g |
| Myristyl myristate | 2 g |
| Sorbitan tristearate | 0.9 g |
| Ethylenediaminetetraacetic acid dipotassium salt | 0.05 g |
| Compound of Example 1 | 1.5 g |
| Phase B | |
| Preservative | qs |
| Glycerol | 3 g |
| Water | 100 g |

The phase A is heated to 85° C. Concomitantly, B is heated to 95° C. The phase B is poured into A and the whole is emulsified in a MORITZ apparatus.

A white cream is obtained.

Example 8

Water-In-Oil Emulsion
Phase A

| | |
|---|---|
| Mixture of magnesium lanolate and liquid paraffin (50:50), sold under the name "MEXANYL GO" by the company CHIMEX | 5.7 g |
| Hydrogenated lanolin | 6.65 g |
| Glyceryl palmitate 2-ethylhexyl ether | 2 g |

Phase B

| | |
|---|---|
| Compound of Example 1 | 3 g |
| Mixture of cetyl/stearyl 2-ethylhexanoate and isopropyl myristate (90:10), sold under the name "PURCELLIN LIQUIDE HUILE 2/066210" by the company DRAGOGO | 3 g |
| | 3 g |

-continued

| | |
|---|---|
| Mixture of lanolin alcohol and liquid paraffin (15:85), sold under the name "LIQUIDE BASE CB1145" by the company CRODA | 3 g |
| Isopropyl palmitate | 4.75 g |
| Liquid paraffin | 7.9 g |
| Petroleum jelly | 15 g |
| Squalane | 0.4 g |
| Mixture of mono-, di- and tri-glycerides of oleic, linoleic, linolenic and stearic acids, sold under the name "VITA COS" by the company KOLMAR | 0.2 g |
| Perfume | 0.8 g |

Phase C

| | |
|---|---|
| Preservative | qs |
| Water | qs 100 g |

The mixture A is heated to 85° C. B is melted at 80° C. B is poured into A. The mixture is cooled to 40° C.

C is added at 40° C. to the above mixture. The whole is cooled three times using a three-cylinder apparatus.

A white cream is obtained.

We claim:

1. Cosmetic or pharmaceutical composition containing, dispersed in an aqueous dispersion phase, vesicles bounded by one or more lamellae composed of a lipid phase containing at least one compound of formula (I):

$$R_f-(CH_2)_{\overline{m}}-S-G_n-H \qquad (I)$$

in which:

$R_f$ denotes a linear $C_6$ to $C_{10}$ perfluoroalkyl radical, m represents 2;

n represents a statistical value or integer between 2 and 3;

G represents a unit chosen from:

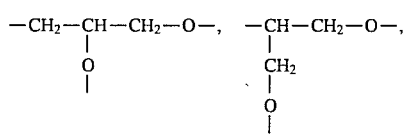

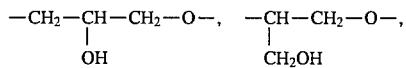

or

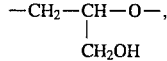

each of the oxygen atoms being linked to a hydrogen atom or to another unit G.

2. Composition according to claim 1, which it contains, in addition, an ionic or nonionic amphiphilic lipid capable of forming stable vesicles, mixed with the compounds of formula (I) to constitute lipid membranes of vesicles.

3. Composition according to claim 1, wherein the vesicles contain at least one cosmetic or dermopharmaceutical active compound in the lipid phase or in the encapsulated phase.

4. Composition according to claim 1, wherein the aqueous phase of dispersion of the vesicles contains at least one water-soluble cosmetic or dermopharmaceutical active compound or at least one amphiphilic active compound.

5. Composition according claim 3, wherein the walls of the vesicles contain at least one fat-soluble cosmetic or dermopharmaceutical active compound.

6. Composition according to claim 5, wherein the aqueous dispersion phase contains a dispersion of droplets of a water-immiscible liquid.

7. Composition according to claim 6, wherein the water-immiscible liquid contains at least one fat-soluble cosmetic or dermopharmaceutical active compound.

8. Composition according to claim 6, wherein the water-immiscible liquid is selected from the group consisting of animal and vegetable oils composed of esters of a fatty acid and of polyols, natural and synthetic essential oils, halogen-containing hydrocarbons, silicones, esters of an inorganic acid and of an alcohol, ethers and polyethers.

9. Composition according to claim 8, characterized in that the cosmetic or dermopharmaceutical active compound is selected from the group consisting of antioxidants and anti-free radical agents, hydrating and humectant agents, melanoregulatory agents which accelerate tanning, depigmenting melanoregulatory agents, skin colouring agents, liporegulators, anti-aging and antiwrinkle agents, anti-UV agents, keratolytic agents, emollients, anti-inflammatory agents, refreshing agents, cicatrizing agents, vascular protective agents, antibacterial agents, antifungal agents, insect-repellant agents, antiperspirant agents, deodorant agents, anti-dandruff agents, agents for combating hair loss, hair colorants, hair bleaching agents, reducing agents for permanent-waving, and skin and hair conditioning agents.

10. Vesicle, characterized in that it is bounded by one or more lamellae composed of a lipid phase containing at least one compound of formula (I):

$$R_f(CH_2)_m\text{—}S\text{—}G_n\text{—}H \qquad (I)$$

in which:

$R_f$ represents a linear $C_6$ to $C_{10}$ perfluoroalkyl radical, m is equal to 2;

n represents a statistical value or integer between 2 and 3; and

G represents a unit $$-CH_2-\underset{\underset{O}{|}}{CH}-CH_2-O-, \quad -\underset{\underset{\underset{O}{|}}{CH_2}}{CH}-CH_2-O-,$$

$$-CH_2-\underset{\underset{OH}{|}}{CH}-CH_2-O-, \quad -\underset{\underset{CH_2OH}{|}}{CH}-CH_2-O-,$$

or $-CH_2-\underset{\underset{CH_2OH}{|}}{CH}-O-,$

\* \* \* \* \*